United States Patent [19]
Shah et al.

[11] Patent Number: 5,891,456
[45] Date of Patent: Apr. 6, 1999

[54] GLYCERYL MONOSTERATE BASED BIODEGRADABLE IMPLANTS FOR SITE-SPECIFIC DELIVERY OF DRUGS

[75] Inventors: Jaymin C. Shah, Mount Pleasant, S.C.; Saleh Allababidi, Rolling Meadows, Ill.

[73] Assignee: Medical University of South Carolina, Charleston, S.C.

[21] Appl. No.: 885,675

[22] Filed: Jun. 30, 1997

[51] Int. Cl.[6] ............................. A61R 2/02; A61K 47/30; A01N 25/12
[52] U.S. Cl. ........................ 424/426; 514/772.3; 514/777
[58] Field of Search ................................ 514/772.3, 777; 424/426

[56] References Cited

U.S. PATENT DOCUMENTS 3,374,146  3/1968  Blicharz et al. .

OTHER PUBLICATIONS

Milojevic et al., "Amylose as a Coating for Drug Delivery to the Colon: Preparation and In Vitro Evaluation Using Glucose Pellets," *Journal of Controlled Release*, 38 (1996) 85–94.

Peri et al., "Development of an Implantable, Biodegradable, Controlled Drug Delivery System for Local Antibiotic Therapy," *Drug Development and Industrial Pharmacy*, 20(8) (1994) 1334–1352.

Nishihata, "Use of Enzymatic Activity for Design of Orally Administered Enteric Dosing Form, " *Journal of Pharmaceutical Pharmacology*, 45 (1993) 947–950.

*Primary Examiner*—Carlos A. Azpuru
*Attorney, Agent, or Firm*—Needle & Rosenberg, P.C.

[57] ABSTRACT

A method to administer a drug locally to a subject in which biodegradable dosage forms that contain the drug are implanted at a localized site beneath the skin of the subject whereupon the dosage forms release the drug over a desired period of time at a substantially continuous rate. Glyceryl monostearate based compositions that accomplish the method are also provided. Compositions are further provided that affect the release profile or release duration of drugs that are released from the compositions, as are methods that employ these varying release profiles to provide implantable dosage forms that release drugs at a prescribed rate over a prescribed period of time. The compositions are particularly well adapted to implantable dosage forms because they biodegrade quickly to an acceptable level after delivering the drug.

53 Claims, 3 Drawing Sheets

RELEASE OF CEFAZOLIN FROM A COMBINATION OF FOUR DEVICES, IN ADDITION TO THE INDIVIDUAL RELEASE PROFILES (ONE UNCOATED AND THREE COATED MATRICES). THE RELEASE PROFILE FROM THE COMBINATION SHOWS A QUASI-LINEAR RELEASE OF CEFAZOLIN FOR 2.5 DAYS.

GLYCERYL MONOSTERATE BASED BIODEGRADABLE IMPLANTS FOR SITE-SPECIFIC DELIVERY OF DRUGS

BACKGROUND OF THE INVENTION

FIELD OF THE INVENTION

This invention relates generally to biodegradable drug dosage forms that can be implanted beneath the skin of mammalian subjects, with particular application to the implantation of such dosage forms at the site of surgical incisions.

Infection at the site of surgical incisions is a common and dangerous hazard associated with surgical operations. Such infection is often controlled and prevented, however, by the systemic administration of antibiotics to the patient after the surgery. These antibiotics are administered both orally in the form of pills, and parenterally, and carried throughout the body and through the bloodstream, with only a fraction of the drug actually reaching the site of the surgical incision and having its intended effect. Because so little of the administered antibiotic actually reaches the site of the surgical incision to prevent infection, much more of the antibiotic than is actually necessary must be prescribed and ingested. Even with these large amounts of prescribed antibiotic, however, infection remains a substantial risk. What is needed is a local method to deliver the antibiotic only to the localized area where the risk of infection is greatest.

Moreover, there is needed a method to deliver the antibiotic locally, in a form other than a liquid solution. While local administration of a drug in solution form provides high local concentration of the drug at the site of the surgical incision, the drug is delivered and absorbed instantaneously, and the effect of the drug therefore quickly diminishes. What is needed, therefore, is a method of locally administering a drug in which the drug is delivered to the local area over an extended period of time.

A biodegradable dosage form which could be implanted at the site of a surgical incision to release a drug over an extended period of time, could be one such method. Such a dosage form, and method of using such dosage form, could be used to deliver many types of drugs in which local delivery of the drug is beneficial.

There is provided by the invention a method to administer a drug locally to a subject in which biodegradable dosage forms that contain the drug are implanted at a localized site beneath the skin of the subject whereupon the dosage forms release the drug over a desired period of time at a substantially continuous rate. Compositions that accomplish the method are also provided. Compositions are further provided that affect the release profile or release duration of drugs that are released from the compositions, as are methods that employ these varying release profiles to provide implantable dosage forms that release drugs at a prescribed rate over a prescribed period of time. The compositions are particularly well adapted to implantable dosage forms because they biodegrade quickly to an acceptable level after delivering the drug.

SUMMARY OF THE INVENTION

In accordance with the purpose(s) of this invention, as embodied and broadly described herein, this invention, in one aspect, relates to a method of delivering a drug to a localized area within a subject comprising implanting dosage forms A and B beneath the skin of the subject at the localized area, wherein dosage forms A and B each comprise a biodegradable core that comprises a drug, wherein dosage forms A and B dissolve and release a treatment effective amount of the drug over separate time periods AT and BT, respectively, and wherein time periods AT and BT may or may not overlap.

The invention further provides a biodegradable implant comprising a mixture comprising, glyceryl monostearate, polyethylene glycol having a molecular weight of from about 4,000 to about 20,000, a surfactant, and a drug.

In yet another aspect, there is provided a combination of biodegradable implants wherein: each implant comprises an inner core comprising a mixture comprising an erosion and/or biodegradation enhancer, glyceryl monostearate ("GMS"), and a drug; one of the implants does not have an outer layer; one of the implants comprises an outer layer comprising glyceryl monostearate and an erosion and/or biodegradation enhancer; one of the implants comprises an outer layer consisting essentially of glyceryl monostearate; and one of the implants comprises an outer layer comprising glyceryl monostearate and an erosion and/or biodegradation enhancer.

Additional aspects and advantages of the invention will be set forth in part in the description that follows, and in part will be obvious from the description, or may be learned by practice of the invention. The advantages of the invention will be realized and attained by means of the elements and combinations particularly pointed out in the concluding claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and, together with the description, serve to explain the principles of the invention.

DESCRIPTION OF THE INVENTION

Figure 1:
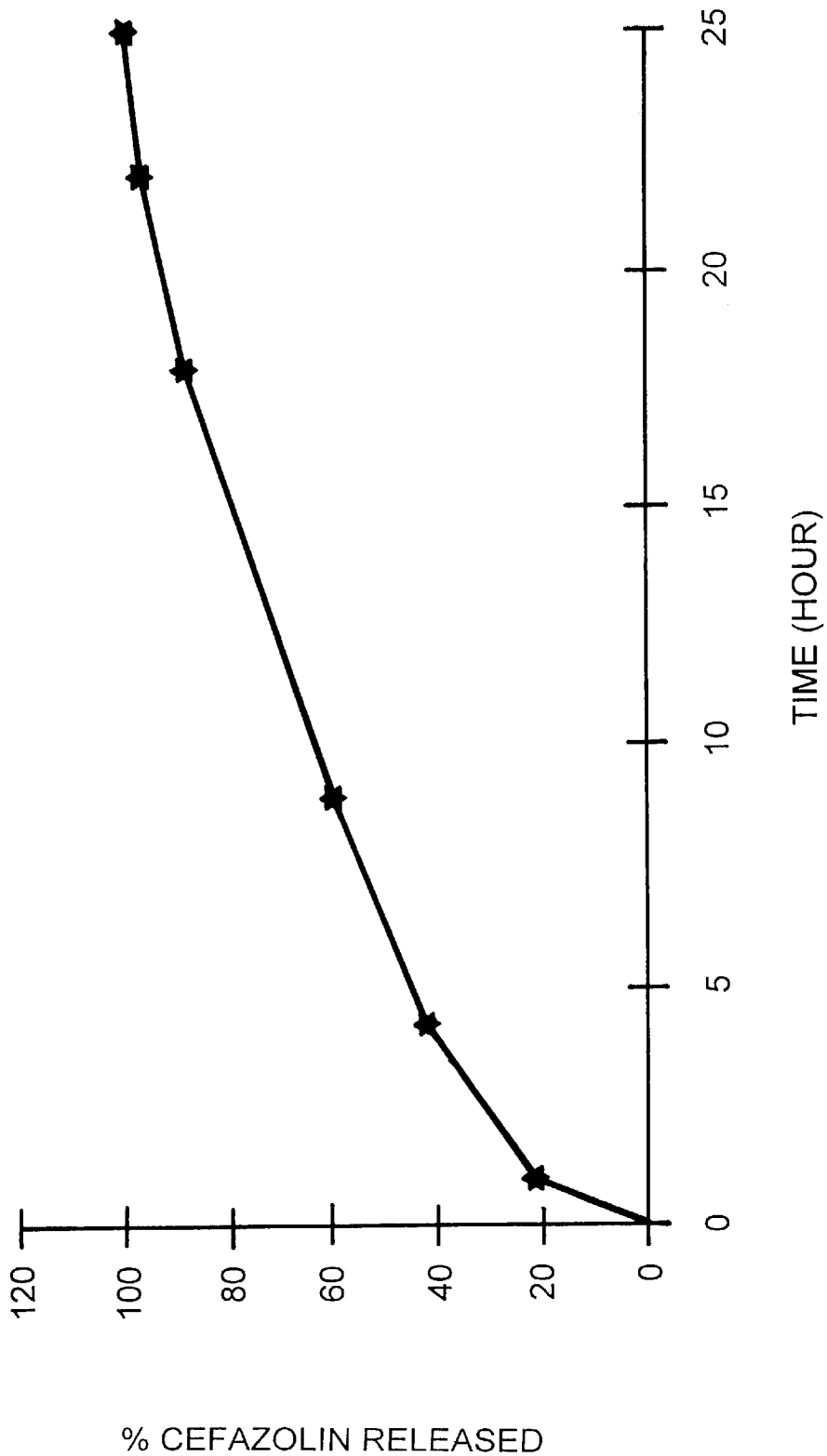
FIG. 1 is a graphical representation of the release profile of cefazolin from an ncoated composition containing 9 parts by weight PEG 8000, 0.1 parts by weight Tween 80, 80.9 parts glyceryl monostearate by weight, and 10 parts by weight cefazolin.

The present invention may be understood more readily by reference to the following description of the invention, the examples included therein, and to the figures and the previous description.

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a hydrophilic constituent" includes mixtures of hydrophilic constituents.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not. For example, the phrase "mixture optionally comprising an erosion enhancer" means that an erosion enhancer may or may not be included and that the description includes both mixtures comprising an erosion enhancer and mixtures not comprising erosion enhancers.

By the term "effective amount" of a compound as provided herein is meant a nontoxic but sufficient amount of the compound to provide the desired effect. As will be pointed out below, the exact amount required will vary from subject to subject, depending on the species, age, and general condition of the subject, the type and severity of the condition that is being treated, the particular compound used, its mode of administration, and the like. Thus, it is not possible to specify an exact "effective amount." However, an appropriate effective amount may be determined by one of ordinary skill in the art using only routine experimentation.

By "pharmaceutically acceptable" is meant a material that is not biologically or otherwise undesirable, i.e., the material may be administered to an individual along with the selected drug without causing any undesirable biological effects or interacting in a deleterious manner with any of the other components of the pharmaceutical composition in which it is contained.

By "drug" is meant any substance, other than food, intended for use in the diagnosis, cure, mitigation, treatment, or prevention of disease in man or other animals.

By "skin" is meant the external coating or investment of a human or other mammal.

By "localized area" is meant a discreet location within the body of a human or other mammal, and beneath the skin of the human or other mammal, that is serviced by the blood stream of the mammal.

By the term "implanting" is meant any method by which a dosage form is artificially deposited beneath the skin of a human or other mammal. Methods of implanting thus include placement of the dosage form within the soft tissue exposed by a surgical incision, and injection of the dosage form by suitable parenteral and laproscopic techniques.

By the term "subject" is meant humans and other mammals in which the invention can be practiced.

By the term "release profile" is meant the graphical representation of percent drug released, plotted on a two dimensional axis against time zero, wherein time zero represents the point at which the one or more dosage forms containing the drug is implanted, or the point at which such implantation is simulated.

By the term "biodegradable" is meant capable of being completely removed from the localized area, by physiological metabolic processes.

By the term "biodegradable" is meant capable of being broken down into smaller particles in the presence of biological fluids.

There is provided by the invention a method of delivering a drug to a localized area within a mammalian subject comprising implanting dosage forms A and B beneath the skin of the subject at the localized area, wherein dosage forms A and B each comprise a biodegradable core that comprises a drug, wherein dosage forms A and B dissolve and release a treatment effective amount of the drug over time periods AT and BT, respectively, that may or may not overlap. There is further provided compositions of dosage forms A and B, and methods for preparing dosage forms A and B.

Dosage forms A and B can be implanted beneath the skin of a subject for many reasons. For example, dosage forms A and B can be implanted beneath the skin of a subject following invasive surgical procedures that require a surgical incision, by placing the dosage forms within the soft tissue exposed by the incision before rejoining the skin with stitches or sutures. While the surgery can be undertaken for the purpose of implanting the dosage forms, and thereby achieving an effective mode of administering the drug, the dosage forms can also be implanted in conjunction with a surgery undertaken for another purpose. For example, the dosage forms can comprise an antibiotic and can be implanted in order to inhibit infection in the area of a surgical incision.

The localized area where the dosage form is implanted can be any area within a subject wherein one desires to locally administer a drug. In chemotherapy for the treatment of cancer, for example, the dosage forms can be implanted proximal to or within the cancerous cells. The method can similarly be used for providing a localized analgesic or anesthetic in conditions such as herniorrhaphy and thoracotomy. Following a surgical procedure, dosage forms comprising antibiotic can be implanted at the location where infection is likeliest. Moreover, the dosage forms can be implanted anywhere within the body that contains biological fluids, and which is serviced by the bloodstream, including within organs, muscle, cartilage, tendon, bone marrow, and any soft tissue. The implants also can be placed into body cavities such as the vagina, uterus, and chest cavity. All of these methods comprise implantation beneath the skin as such term is used in the claims and this application.

The method of implantation also can vary depending upon the reason for delivering drugs to the subject. Thus, while the dosage forms are often implanted in order to prevent infection by physically positioning the dosage forms within soft tissue exposed by a surgical incision, the forms also can be implanted by parenteral injection through subdermal injection and laproscopic techniques.

Because most treatment or prophylactic regimes involving drug administration require a substantially constant delivery of drugs to the subject, the method of this invention is typically practiced in a manner which delivers the drug at a substantially continuous rate after the period of implantation. The following discussion relates most particularly, therefore, to methods and compositions capable of delivering drugs at a substantially continuous rate from time zero. Modifications and variations of the method and composition can, however, be made to tailor the release profile of the dosage forms if continuous release is not desired, or if one does not desire to initiate drug delivery at time zero. The invention encompasses all such modifications and variations. Moreover, while the following discussion refers generally to dosage forms having only one drug, the methods and compositions of this invention are capable of delivering more than one drug by appropriate modification.

A typical method to achieve substantially continuous rates from time zero is to employ two or more dosage forms that release the drug at substantially the same rate, but which release the drug over substantially distinct time periods. For example, in a two dosage form method, as the release of drug from dosage form A is ending at the close of time period AT, the release of drug from dosage form B is beginning, at the initiation of time period BT. These time periods often are not entirely discreet, and the start and end point of the release from each of the dosage forms is not necessarily discreetly defined. This is acceptable, however, because all that is needed is that the drug is released from the combination, at the desired release profile, over the desired time and at the desired rate.

One way to obtain a substantially continuous release profile is to employ dosage forms sharing a similar-or common core that contains the drug, wherein one or more of the dosage forms is not coated with an outer layer, and one of the dosage forms is coated with an outer layer composition that substantially dissolves and exposes the core at the end of the release period for the other dosage form. By substantially dissolves is meant that the coating dissolves sufficiently to expose the core and thereby allow the core to begin releasing drug at a rate and time that meets the criteria for the relevant administration regime. The weight of the cores, and the precise ratios of compositions in the cores need not be identical, and can vary significantly. Dosage forms A and B should, however, each contain a similar core, releasing the drug over substantially similar time periods AT and BT respectively, with only dosage form B having an outer layer. By similar core is meant comprising substantially equivalent constituents that allow the drug to be released at substantially the same rate, for substantially the same time. The outer layer for dosage form B can then be formulated so as to dissolve and expose the core from dosage form B at about the end of time period AT. Because a similar core is employed, each of the dosage forms releases the drug at about the same rate and for about the same period of time, to provide a substantially continuous rate of release, and thereby effectively doubling the release time for the uncoated dosage form alone.

Additional dosage forms can also be employed to extend the cumulative period of release beyond the end of time period BT by, for example, formulating an outer layer for another dosage form C that substantially dissolves and exposes the core composition of the dosage form C at the end of time period BT. Additional dosage forms can be formulated, employing these concepts, to extend the time of release even further. Alternatively, dosage forms can be formulated to deliver drugs at varying intervals after implantation. As further described below, the constituents of the core composition can also be manipulated to control the time period of drug release.

Many suitable compositions for the core are known and can be used in practicing the invention. Such compositions are described in, for example, Chasin et. al., *Biodegradable Polymers as Drug Delivery Systems*, Marcel Dekker Inc., NY, ISBN 0-8247-8344-1, the disclosure of which being incorporated herein by this reference. Preferable core compositions are pharmaceutically acceptable, biodegradable, and biodegradable, and meet the particular release profile characteristics that are required to achieve the administration regime involved. More preferred core compositions are completely biodegradable, and even more preferred core compositions biodegrade completely shortly after release of the drug has effectively terminated, i.e., shortly after a sufficient quantity of the drug from the core composition has released in order to achieve the desired effect. By shortly after is meant within a period of time that does not interfere substantially with the release and biodegradation of other dosage forms, or with the natural physiologic processes within the localized area.

The core composition typically comprises a base composition which acts as a matrix to contain and hold the contents of the core composition together. The base composition can, in turn, comprise one or more constituents.

A particularly suitable core composition for the dosage forms of the present invention comprises a glyceryl monostearate base. Glyceryl monostearate is particularly suitable because it is a natural product commonly found in animal fat and hydrogenated vegetable oils. Glyceryl monostearate is therefore biocompatible, having well defined metabolic pathways. It is involved in the biosynthesis of lipids, and is known to safely deposit in the human metabolism and be absorbed into and excreted from the bloodstream.

The core composition optionally can comprise erosion and biodegradation enhancers which facilitate the erosion of the matrix, the dissolution of the core composition, or the uptake of the core composition via metabolic processes. Particularly suitable erosion and biodegradation enhancers are biodegradable in biological fluids, and biocompatible. In one suitable embodiment the core composition contains one or more hydrophilic constituents, that generally are capable of enhancing the erosion of the core base composition, or matrix constituent, in the presence of biological fluids. Without wishing to be bound by any particular theory, it is believed that hydrophilic constituents are quickly released from the matrix of the core composition when exposed to biological fluids, leaving behind pores and channels for the biological fluids to penetrate the matrix and thereby to enhance the erosion of the matrix and the release of drug from the matrix.

Any pharmaceutically acceptable hydrophilic constituent may be contained in the core composition to achieve the desired effect. Suitable hydrophilic constituents are described, for example, in Wade & Weller, *Handbook of pharmaceutical Excipients* (London: Pharmaceutical Press; Washington D.C.: American Pharmaceutical Ass'n 1995) the disclosure from which being hereby incorporated by this reference. Preferred constituents are typically capable of being incorporated into a dry powder so that they can subsequently be incorporated into the dosage form by compression techniques. Preferred hydrophilic constituents are the polyethylene glycols ("PEGs"), propylene glycol ("PG"), glycerin, and sorbitol. A particularly preferred hydrophilic constituent is polyethylene glycol having a molecular weight preferably between about 4,000 and 20,000, and even more preferably of about 8,000 ("PEG 8000").

The core composition also may optionally contain a surfactant that will further enhance the erosion of the matrix and the release of the drug. Surfactants are generally capable of increasing the wettability and the solubility of composition bases such as glyceryl monostearate in biological fluids, and thereby to cause the disintegration and to enhance the erosion of the glyceryl monostearate after the dose form has been implanted. Surfactants can also help to break down the core composition matrix when, for example, the method of forming the dosage form has reduced the solubility of any of the constituents. Surfactants can also improve the uptake of the dosage forms into the bloodstream. Many particularly suitable surfactants are known which can be incorporated into the core composition, and are generally known to workers skilled in the art. Nonionic surfactants are, however, typically preferred. Preferred surfactants also are biodegradable and biocompatible. Particularly preferred surfactants include glyceryl based surfactants such as glyceryl monooleate and glyceryl monolaurate, polaxemers such as Pluronic F127, and polysorbates such as polyoxyethylene sorbitan monooleate ("Tween 80"). Of these, Tween 80 is especially preferred.

Any drug can be included in the core composition that one wishes to deliver through the implants of the invention. Antibiotics are particularly suitable for incorporation into the core composition in order to treat or prevent infections associated with invasive surgery. Particularly suitable antibiotics for such implants include, for example, cefazolin, ciprofloxacin, and vancomycin. Of these, a more preferred antibiotic is cefazolin.

The amount of drug included in the dosage forms is determined by the total amount of the drug to be administered, the rate at which the drug is to be delivered, and the number of dosage forms to be used. The total amount of the drug to be delivered is determined according to clinical requirements, and in keeping with the considerations that typically inform drug dosage determinations in other contexts. However, in the present method and with the present compositions, the ideal drug release profile can be achieved.

The proportion and types of constituents contained in the core composition often affect the release profile of the core composition, the biodegradability of the core composition, and the time required for the core composition to biodegrade completely. Any proportions or types of constituents can be chosen that effectively achieve the desired release profile, and thereby carry out the prescribed administration regime. The most desirable core compositions generally release the drug substantially continuously, and biodegrade completely shortly after substantially all of the drug has been effectively released. Moreover, compositions that release the drug over a greater period of time are often preferred. The core compositions, in conjunction with the selected outer coatings, provide a great deal of flexibility in designing and implementing a drug administration regime.

In a particular embodiment the core composition comprises from zero to about 20 parts by weight erosion and/or biodegradation enhancers, from about 60 to about 100 parts by weight core base composition, and from about 1 to about 40 parts by weight drug. A preferred core composition comprises from about 1 to about 15 parts by weight hydrophilic constituent; from about 60 to about 100 parts by weight core base composition; from about 0 to about 1 parts by weight surfactant; and from about 1 to about 30 parts by weight drug. A more preferred core composition comprises from about 1 to about 13 parts by weight hydrophilic constituent; from about 80 to about 95 parts by weight core base composition; from about 0 to about 0.12 parts by weight surfactant; and from about 5 to about 25 parts by weight drug.

As previously noted, the core composition can be coated with a composition which delays the release of drug from the core composition, by shielding the core composition from the biodegrading forces of biological fluids until the outer layer has itself dissolved. Moreover, the coating composition can be chosen or modified in order to obtain a dosage form that begins releasing drug at a designated time after the dosage form has been implanted. Preferred outer layer compositions are bioerodable and biodegrade.

There are, of course, many suitable base constituents for the outer layer, or "outer base composition." Such compositions are described in, for example, Chasin et. al., *Biodegradable Polymers as Drug Delivery Systems*, Marcel Dekker Inc., NY, ISBN 0-8247-8344-1, the disclosure of which being incorporated herein by this reference. A particularly suitable outer base composition, is glyceryl monostearate, again because it is biodegradable and biocompatible. The composition for the outer layer can also comprise additional constituents that modify the biodegradation properties of the outer layer, including the rate at which the outer layer dissolves, and the time at which the outer layer biodegrades sufficiently to expose the inner core to biological fluids. The composition for the outer layer could, for example, contain an erosion or biodegradation enhancer, such as the ones suitable for the core composition. Hydrophilic constituents, which typically would increase the rate at which the outer layer dissolves, are particularly suitable for this purpose.

Suitable hydrophilic constituents are described, for example, in the *Handbook of Pharmaceutical Excipients*, the disclosure from which being hereby incorporated by reference. Preferred hydrophilic constituents for the outer layer are polyethylene glycol, glycerol, sorbitol, and propylene glycol. A more preferred hydrophilic constituent is polyethylene glycol having a molecular weight of from about 4,000 to about 20,000, and most preferably of about 8000.

The outer layer could also include components that retard the rate at which the outer layer erodes or biodegrades (erosion and/or biodegradation retardants). Hydrophobic constituents are a particularly suitable class of components for retarding the rate at which the outer layer biodegrades. Suitable hydrophobic constituents are described, for example, in the *Handbook of Pharmaceutical Excipients*, the disclosure from which being hereby incorporated by reference. Of the hydrophobic constituents, oil based products are preferred, with peanut oil and olive oil being more preferred, and castor oil being especially preferred.

The weight of the outer layer in relation to the weight of the core can also be manipulated in order better to time the inception of release from a particular dosage form, and thereby to maintain a substantially continuous rate of drug release from a combination of dosage forms. In a preferred embodiment the weight ratio of the outer layer to the weight of its respective biodegradable core is from about 1:1 to about 4:1. In a more preferred embodiment, the ratio of the weight of the outer layer to the weight of the biodegradable core is from about 2:1 to about 3:1.

In one method of practicing the invention two dosage forms A and B are employed, wherein dosage form A does not have an outer layer and dosage form B comprises a biodegradable outer layer BO. Dosage forms A and B may each comprise common core compositions and weigh about the same. Alternatively, dosage forms A and B may have different weights and may also comprise constituents at different ratios. In such a method a particularly suitable biodegradable outer layer BO comprises glyceryl monostearate and a hydrophilic constituent. A preferred hydrophilic constituent for the outer layer BO composition in such a method is polyethylene glycol, glycerol, sorbitol, or propylene glycol. An even more preferred hydrophilic constituent is polyethylene glycol having a molecular weight of about between about 4,000 and 20,000, and most preferably having a molecular weight of about 8,000.

The outer layer BO may preferably comprise from about 95 to about 99.9 parts by weight glyceryl monostearate, and from about 0.1 to about 5 parts by weight hydrophilic constituent, and even more preferably may comprise from about 97 to about 99.5 parts by weight glyceryl monostearate; and from about 0.5 to about 3 parts by weight polyethylene glycol having a molecular weight of about 8000.

In another method a third dosage form C is employed which is designed to begin releasing drug when dosage form B stops effectively releasing drug. In such a method dosage form C may preferably comprise a biodegradable outer layer CO and the same biodegradable core as dosage form B. The outer layer CO may optionally comprise an erosion or biodegradation enhancer or retardant, as needed to achieve the desired release profile. The outer layer preferably consists essentially of a suitable base composition, which even more preferably is glyceryl monostearate.

In yet another method a fourth dosage form D is implanted along with the other dosage forms, and is designed to begin releasing drug when dosage form C stops effectively releasing drug. In such a method dosage form D may preferably comprise an outer layer DO and the same biodegradable core as dosage forms B, and C. In such a method the biodegradable outer layer DO preferably comprises glyceryl monostearate and a suitable erosion and/or biodegradation retardant, preferably a hydrophobic constituent. A preferred hydrophobic constituent is an oil based constituent such as olive oil, or peanut oil, with castor oil being most preferred. Outer layer DO may preferably comprise from about 95 to about 99.9 parts by weight glyceryl monostearate and from about 0.1 to about 5 parts by weight hydrophobic constituent. Outer layer DO may even more preferably comprise from about 96 to about 99.5 parts by weight glyceryl monostearate and from about 0.5 to about 4 parts by weight castor oil.

The method can also be carried out with any lesser combination of the above dosage forms. For example, dosage forms B and C can be employed to provide a delayed release profile, dosage forms B, C and D can be employed to provide a delayed yet more sustained release of drug, and dosage forms C and D can be employed to provide an even more delayed release of drug.

The compounds of the invention may be conveniently formulated into pharmaceutical compositions composed of one or more of the compounds in association with a pharmaceutically acceptable carrier. See, e.g., *Remington's Pharmaceutical Sciences*, latest edition, by E. W. Martin Mack Pub. Co., Easton, Pa., which discloses typical carriers and conventional methods of preparing pharmaceutical compositions that may be used in conjunction with the preparation of formulations of the inventive compounds and which is incorporated by reference herein. Of the methods for preparing pharmaceutical compositions of the present invention, however, the compression method is most preferred.

The compositions may be in any form by which the functions of the invention can be accomplished including, for example, solid and semi-solid dosage forms such as, for example, tablets, pills, and capsules. The compositions will include, as noted above, an effective amount of the selected drug in combination with a pharmaceutically acceptable and biodegradable carrier and, in addition, may include other medicinal agents, pharmaceutical agents, carriers, adjuvants, diluents, etc.

EXAMPLES

The following examples are put forth so as to provide those of ordinary skill in the art with a complete disclosure and description of how the compounds claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in °C. or is at room temperature, and pressure is at or near atmospheric.

Example 1

Preparation of Antibiotic Loaded Devices by the Compression Method

The devices were prepared according to the following steps and procedures:

1. Mixing of Glyceryl Monostearate with the Erosion/Biodegradation Enhancer(s):

89.9 parts glyceryl monostearate (GMS), 10 parts PEG 8000, and 0.1 parts Tween 80 were heated to 5° C. above the melting point of glyceryl monostearate (69° C.) in a water bath, while stirring with a glass rod. The molten blend was removed from the water bath and allowed to cool to room temperature, while mixing until the molten mass solidified. The solidified blend was kept at room temperature for 10 minutes, then stored in the freezer before any further processing.

2. Milling of the Glyceryl monostearate Based Blend:

The frozen mass of the glyceryl monostearate based blend was loaded into a Micro-Mills® grinder along with dry ice. The mass was milled for 30–60 seconds resulting in a very fine powder. Dry ice was added to prevent over heating and consequent melting of the milled mass.

3. Loading the Antibiotic:

Sufficient quantities of cefazolin to obtain 10% by weight cefazolin blends, and 20% by weight cefazolin blends, were added to portions of the powdered glyceryl monostearate based blend and mixed for 30 minutes in a V-mixer. Three random samples were obtained from each of the powder blends after mixing to test for content uniformity. The results of the three samples were averaged and the relative standard deviation (RSD) was determined. Batches with RSD>10% were rejected and the powder was re-mixed and assayed for content uniformity.

4. Compression of the Blend:

60 milligrams of the antibiotic loaded blend containing 20% by weight cefazolin from the previous step was compressed into a tablet shaped device, using a Carver Laboratory Press. 200 milligrams of the antibiotic loaded blend containing 10% cefazolin by weight was similarly compressed into a tablet shaped device.

5. Optional Dry Coating of the tablet shaped devices:

The 60 milligram tablet shaped devices from step 4 were coated with 150 mg. of glyceryl monostearate based materials using the dry coating technique. The coating material was glyceryl monostearate based, prepared by combining glyceryl monostearate with other excipients in the same procedure described in steps 1 and 2 above. The dry coating process was conducted according to the following general procedure: ⅓ of the total coating material was placed in the die over the lower punch and manually compressed to level this first layer. The core was placed in the center of the die over the first layer. The remaining (⅔) of the coating material was placed on top of the core and compressed using a Carver Press at a pressure of 1 metric ton.

Release Studies

The dosage forms were tested using the following procedures.

1. Vial Method:

The vial method was used to study the release of cefazolin from the glyceryl monostearate based devices. The glyceryl monostearate based devices were individually placed into 20 ml glass vials with 15 ml phosphate buffer (0.1M, pH 7.4) and agitated at 60 oscillations per minute in a horizontal water bath shaker at 37° C. The release medium was replaced with fresh solution each time a sample was withdrawn. Samples were collected at different time intervals, filtered (3 μm membrane), appropriately diluted to fit into the range of the calibration curve, then assayed for cefazolin. All the studies were conducted in triplicates.

2. Assay:

Both UV and HPLC assays were used for the determination of cefazolin concentrations in the samples.

Results

Figure 2:
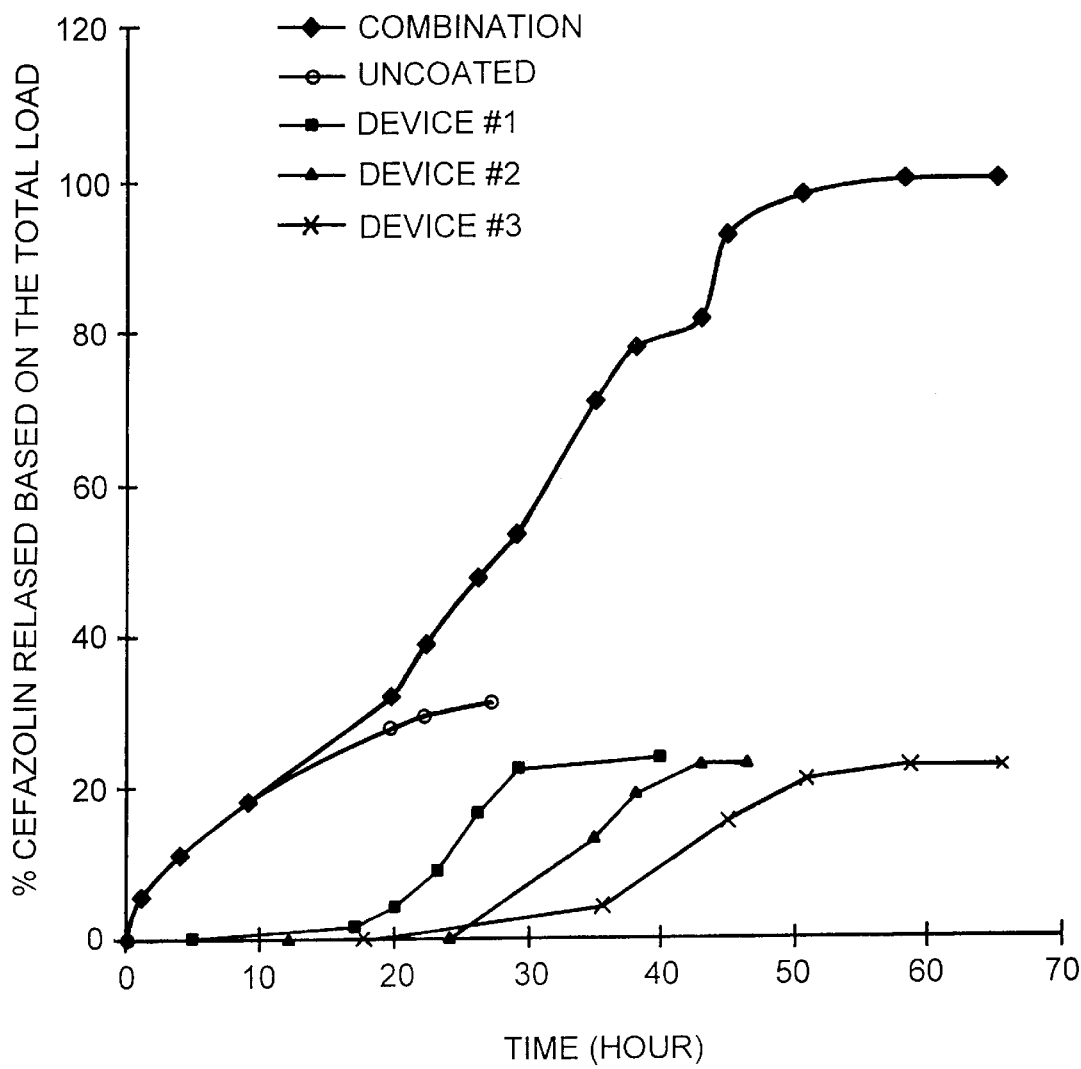
FIG. 2 is a graphical representation of the cumulative release profile of cefazolin from a combination of four devices, in addition to the individual release profiles of the four devices. The four devices are: (1) 200 milligrams of an uncoated composition containing 10 parts by weight cefazolin, 9 parts by weight PEG 8000, 0.1 parts by weight Tween 80, and 80.9 parts GMS by weight, (2) 60 milligrams of a composition containing 20 parts by weight cefazolin, 8 parts by weight PEG 8000, 0.1 parts by weight Tween 80, and 71.9 parts GMS by weight, coated with 150 milligrams of a composition containing 99 parts by weight GMS and 1 part by weight PEG 8000, (3) 60 milligrams of a composition containing 20 parts by weight cefazolin, 8 parts by weight PEG 8000, 0.1 parts by weight Tween 80, and 71.9 parts GMS by weight, coated with 150 milligrams of a composition only containing GMS, and (4) 60 milligrams of a composition containing 20 parts by weight cefazolin, 8 parts by weight PEG 8000, 0.1 parts by weight Tween 80, and 71.9 parts GMS by weight, coated with 150 milligrams of a composition containing 98 parts by weight GMS, and 2 parts by weight castor oil.

The combination of 4 devices; one uncoated and three coated, provided a release duration of 2.5 days in vitro (FIG. 2). The composition of the outer coating of the devices is listed in table (I). Each of the devices had a different release onset based on the composition of the coating material. Table II summarizes the in vitro cefazolin release onset and duration from the different coated and uncoated devices. The total in vitro release duration from all the devices was 60 hours. All the matrices completely disintegrated and turned into a slurry (suspension) in the release medium within 3–5 hours of releasing all their cefazolin load.

TABLE I

| Device # | Core Weight (mg) | Coating Composition (% W/W) | Coating Weight (mg) |
|---|---|---|---|
| 1 | 200 | No Coating | N/A |
| 2 | 60 | GMS:PEG 8000 (99:1) | 150 |
| 3 | 60 | GMS 100 | 150 |
| 4 | 60 | GMS:Castor Oil (98:2) | 150 |

TABLE II

| Device # | Onset of Release (hour) | Termination of Release (hour) |
|---|---|---|
| uncoated | 0 | 25 |
| 1 | 18 | 30 |
| 2 | 24 | 42 |
| 3 | 36 | 60 |

Example 2

Glyceryl Monostearate Based Devices for the Delivery of Ciprofloxacin

Ciprofloxacin devices were prepared according to the procedures in Example 1 that contained 10 parts by weight ciprofloxacin, 80.9 parts glyceryl monostearate (GMS), 9 parts PEG 8000, and 0.1 parts Tween 80. The release of ciprofloxacin was studied in a USP ("The United States Pharmacopeia") dissolution apparatus II (paddle method at 50 rpm) at 37° C. in 0.5 liter 0.1M phosphate buffer (pH 7.4). The concentration of cefazolin was determined by HPLC assay. The study was conducted in triplicates.

Figure 3:
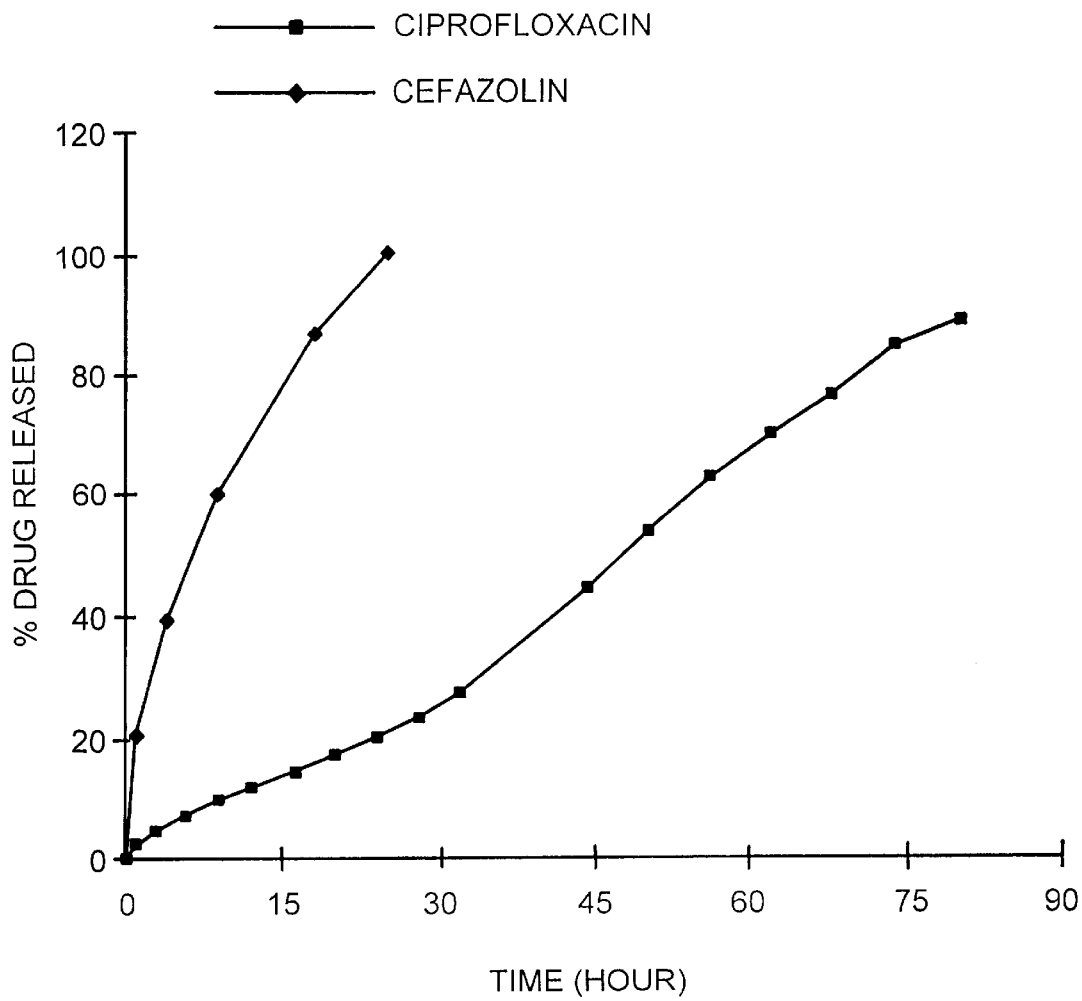
FIG. 3 is a comparison of the release profiles and duration of cefazolin and ciprofloxacin release from identical glyceryl monostearate based compositions.

An 80 hour release duration was achieved. The release duration of ciprofloxacin was longer than that of cefazolin from identical matrix formulation (FIG. 3). This can be explained by the lower solubility of ciprofloxacin compared to cefazolin (0.16 vs. 325 mg/ml).

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of delivering a drug to a localized area within a subject comprising implanting dosage forms A and B beneath the skin of the subject at the localized area, wherein dosage forms A and B comprise biodegradable cores AC and BC respectively that comprise a drug and glyceryl monostearate, and wherein dosage forms A and B dissolve and release a treatment-effective amount of the drug over time periods AT and BT, respectively.

2. The method of claim 1 wherein time periods AT and BT overlap.

3. The method of claim 1, wherein dosage forms A and B dissolve and release the treatment-effective amount of the drug at a substantially continuous rate over time periods AT and BT.

4. The method of claim 1, wherein dosage form B further comprises a biodegradable outer layer BO.

5. The method of claim 4, wherein the biodegradable outer layer BO dissolves substantially at the inception of time period BT to expose the contents of the biodegradable core, which releases drug at a substantially continuous rate over time period BT.

6. The method of claim 1, wherein dosage forms A and B comprise biodegradable outer layers AO and BO respectively, each comprising glyceryl monostearate.

7. The method of claim 6 wherein the biodegradable core is similar for dosage forms A and B.

8. The method of claim 6, wherein outer layer AO further comprises a hydrophilic constituent.

9. The method of claim 8 wherein the hydrophilic constituent comprises polyethylene glycol, glycerol, sorbitol, or propylene glycol.

10. The method of claim 9, wherein the hydrophilic constituent is polyethylene glycol having a molecular weight of from about 4,000 to about 20,000.

11. The method of claim 6, wherein biodegradable outer layer BO further comprises a hydrophobic constituent.

12. The method of claim 6 wherein the hydrophobic constituent is oil-based.

13. The method of claim 12 wherein the hydrophobic constituent is castor oil.

14. The method of claim 1, wherein dosage form A does not have an outer layer, and wherein dosage form B comprises a biodegradable outer layer BO.

15. The method of claim 14 wherein biodegradable outer layer BO comprises glyceryl monostearate and a hydrophilic constituent.

16. The method of claim 15 wherein the hydrophilic constituent comprises polyethylene glycol, glycerol, sorbitol, or propylene glycol.

17. The method of claim 15, wherein the hydrophilic constituent is polyethylene glycol having a molecular weight of from about 4,000 to about 20,000.

18. The method of claim 14, further comprising implanting a dosage form C within the subject at the localized area, wherein dosage form C comprises a biodegradable core and biodegradable outer layer CO, wherein the biodegradable core for dosage form C comprises the drug and glyceryl monostearate, and wherein biodegradable outer layer CO consists essentially of glyceryl monostearate.

19. The method of claim 18, further comprising implanting a dosage form D within the subject at the localized area, wherein dosage form D comprises a biodegradable core and biodegradable outer layer DO, wherein the biodegradable core for dosage form D comprises the drug and glyceryl monostearate, and wherein biodegradable outer layer DO comprises glyceryl monostearate and a hydrophobic constituent.

20. The method of claim 1, wherein the biodegradable core is a mixture that further comprises one or more erosion and/or biodegradation enhancers.

21. The method of claim 20, wherein the erosion and/or biodegradation enhancer comprises a hydrophilic constituent.

22. The method of claim 21, wherein the hydrophilic constituent is polyethylene glycol having a molecular weight of from about 4,000 to about 20,000.

23. The method of claim 20 wherein the erosion and/or biodegradation enhancer comprises a surfactant.

24. The method of claim 23, wherein the surfactant is polyoxyethylene sorbitan monooleate.

25. The method of claim 20, wherein the drug is an antibiotic.

26. The method of claim 25 wherein the antibiotic is cefazolin.

27. The method of claim 1, wherein the biodegradable core is a mixture that comprises:
   (a) from about 1 to about 15 parts by weight hydrophilic constituent;
   (b) from about 60 to about 100 parts by weight glyceryl monostearate;
   (c) up to about 1 part by weight surfactant; and
   (d) from about 1 to about 30 parts by weight drug.

28. The method of claim 1, wherein the biodegradable core is a mixture that comprises:
   (a) from about 1 to about 13 parts by weight polyethylene glycol having a molecular weight of from about 4,000 to about 20,000;
   (b) from about 80 to about 95 parts by weight glyceryl monostearate;
   (c) up to about 0.12 parts by weight polyoxyethylene sorbitan monooleate; and
   (d) from about 5 to about 25 parts by weight cefazolin.

29. The method of claim 6, wherein outer layer AO comprises:
   (a) from about 95 to about 99.9 parts by weight glyceryl monostearate; and
   (b) from about 0.1 to about 5 parts by weight hydrophilic constituent.

30. The method of claim 6, wherein outer layer AO comprises:
   (a) from about 97 to about 99.5 parts by weight glyceryl monostearate; and
   (b) from about 0.5 to about 3 parts by weight polyethylene glycol having a molecular weight of from about 4,000 to about 20,000.

31. The method of claim 8, wherein outer layer BO comprises:
   (a) from about 95 to about 99.9 parts by weight glyceryl monostearate; and
   (b) from about 0.1 to about 5 parts by weight hydrophobic constituent.

32. The method of claim 30, wherein outer layer BO comprises:
   (a) from about 96 to about 99.5 parts by weight glyceryl monostearate; and
   (b) from about 0.5 to about 4 parts by weight castor oil.

33. The method of claim 6, wherein the ratio of the weight of outer layer AO to the weight of biodegradable core AC, and the ratio of the weight of outer layer BO to biodegradable core BC, is from about 1:1 to about 4:1.

34. The method of claim 32, wherein the ratio of the weight of outer layer AO to the weight of biodegradable core AC, and the ratio of the weight of outer layer BO to biodegradable core BC, is from about 2:1 to about 3:1.

35. The method of claim 1, wherein the localized area comprises the site of a surgical incision.

36. A method of preventing infection in a localized area within a subject comprising implanting dosage forms A and B beneath the skin of the subject at the localized area, wherein dosage forms A and B each comprise a biodegradable core that comprises a drug and glyceryl monostearate, and wherein dosage forms A and B dissolve and release a treatment-effective amount of the drug over time periods AT and BT, respectively.

37. The implant comprising a core mixture comprising glyceryl monostearate, one or more biodegradation and/or erosion enhancers, and a drug, wherein the one or more biodegradation and/or erosion enhancers comprise a surfactant.

38. The implant comprising a core mixture comprising glyceryl monostearate, one or more biodegradation and/or erosion enhancers, and a drug, further comprising a coating.

39. The implant of claim 38 wherein the one or more biodegradation and/or erosion enhancers comprise a surfactant.

40. The implant of claim 37 wherein the drug comprises cefazolin.

41. The implant of claim 37 wherein the biodegradation and/or erosion enhancers comprise a hydrophilic constituent and a surfactant.

42. The implant of 41 claim wherein the surfactant comprises polyoxyethylene sorbitan monooleate and the hydrophilic constituent comprises polyethylene glycol having a molecular weight of from about 4,000 to about 20,000.

43. The implant of claim 37 comprising a mixture comprising:
   (a) from about 1 to about 15 parts by weight polyethylene glycol having a molecular weight of from about 4,000 to about 20,000;
   (b) from about 60 to about 95 parts by weight glyceryl monostearate;

(c) up to about 1 parts by weight surfactant; and (d) from about 1 to about 30 parts by weight drug.

44. The implant of claim 37 comprising a mixture comprising:
- (a) from about 1 to about 13 parts by weight polyethylene glycol having a molecular weight of about 4,000 to about 20,000;
- (b) from about 80 to about 95 parts by weight glyceryl monostearate;
- (c) up to about 0.12 parts by weight polyoxyethylene sorbitan monooleate; and
- (d) from about 5 to about 25 parts by weight cefazolin.

45. The implant of claim 37, further comprising an outer layer comprising:
- (a) from about 95 to about 99.9 parts by weight glyceryl monostearate; and
- (b) from about 0.1 to about 5 parts by weight hydrophilic constituent.

46. The implant of claim 45 wherein the hydrophilic constituent comprises polyethylene glycol having a molecular weight of from about 4,000 to about 20,000.

47. The implant of claim 37, further comprising an outer layer consisting essentially of glyceryl monostearate.

48. The implant of claim 37, further comprising an outer layer comprising:
- (a) from about 95 to about 99.9 parts by weight glyceryl monostearate; and
- (b) from about 0.1 to about 5 parts by weight hydrophobic constituent.

49. The implant of claim 48, wherein the hydrophobic constituent comprises castor oil.

50. The implant of claim 45, wherein the ratio of the weight of the outer layer to the weight of the biodegradable core is from about 1:1 to about 4:1.

51. The implant of claim 47, wherein the ratio of the weight of the outer layer to the weight of the biodegradable core, is from about 1:1 to about 4:1.

52. The implant of claim 48, wherein the ratio of the weight of the outer layer to the weight of the biodegradable core is from about 1:1 to about 4:1.

53. A kit comprising a combination of biodegradable implants wherein:
- (a) each implant comprises an inner core comprising a mixture comprising an erosion and/or biodegradation enhancer, glyceryl monostearate, and a drug;
- (b) one of the implants does not have an outer layer;
- (c) one of the implants comprises an outer layer comprising glyceryl monostearate and an erosion and/or biodegradation enhancer;
- (d) one of the implants comprises an outer layer consisting essentially of glyceryl monostearate; and
- (e) one of the implants comprises an outer layer comprising glyceryl monostearate and an erosion and/or biodegradation retardant.

* * * * *